United States Patent
Tabata et al.

(10) Patent No.: US 10,078,210 B2
(45) Date of Patent: Sep. 18, 2018

(54) LIGHT SOURCE APPARATUS

(71) Applicant: OLYMPUS CORPORATION, Tokyo (JP)

(72) Inventors: Motoki Tabata, Hino (JP); Masahiro Nishio, Hachioji (JP); Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 313 days.

(21) Appl. No.: 14/996,433

(22) Filed: Jan. 15, 2016

(65) Prior Publication Data

US 2016/0131892 A1 May 12, 2016

Related U.S. Application Data

(63) Continuation of application No. PCT/JP2014/067232, filed on Jun. 27, 2014.

(30) Foreign Application Priority Data

Jul. 17, 2013 (JP) .................................. 2013-148454

(51) Int. Cl.
*A61B 1/06* (2006.01)
*G02B 23/24* (2006.01)
(Continued)

(52) U.S. Cl.
CPC ............ *G02B 23/2469* (2013.01); *A61B 1/06* (2013.01); *F21K 9/20* (2016.08); *F21K 9/61* (2016.08);
(Continued)

(58) Field of Classification Search
CPC ............ G02B 23/2469; G02B 27/1006; H05B 33/0869; H05B 33/086; F21K 9/61;
(Continued)

(56) References Cited

U.S. PATENT DOCUMENTS

2006/0251408 A1  11/2006  Konno et al.
2011/0069161 A1*  3/2011  Ozawa ................. A61B 1/0638
                                                              348/68
(Continued)

FOREIGN PATENT DOCUMENTS

EP  2 301 412 A1  3/2011
EP  2 733 515 A1  5/2014
(Continued)

OTHER PUBLICATIONS

Chinese Office Action dated Nov. 30, 2016 in related Chinese Patent Application No. 201480040053.4.
(Continued)

*Primary Examiner* — Sathyanaraya V Perungavoor
*Assistant Examiner* — Howard D Brown, Jr.
(74) *Attorney, Agent, or Firm* — Scully, Scott, Murphy & Presser, P.C.

(57) ABSTRACT

A light source apparatus includes a main unit, light source modules attachable to and detachable from the main unit, and storage mediums storing characteristic information of the light source modules. Each light source module includes at least one light source and a light connection part to be optically connected to the main unit. The main unit includes entrance parts to be optically connected to the light connection parts of the connected light source modules, a light combining unit to combine light entering the entrance parts, at least one exit part to cause light combined by the light combining unit to exit, and an exit light characteristic deriving unit to derive characteristic information of achievable exit light based on characteristic information of the light source modules stored in the storage mediums.

25 Claims, 7 Drawing Sheets

(51) Int. Cl.

| | | |
|---|---|---|
| *G02B 27/10* | (2006.01) | |
| *H04N 5/225* | (2006.01) | |
| *F21K 9/20* | (2016.01) | |
| *F21K 9/61* | (2016.01) | |
| *H05B 33/08* | (2006.01) | |
| *H01L 33/60* | (2010.01) | |
| *F21Y 115/30* | (2016.01) | |
| *F21Y 115/10* | (2016.01) | |

(52) U.S. Cl.
CPC ....... *G02B 27/1006* (2013.01); *H04N 5/2256* (2013.01); *H05B 33/086* (2013.01); *H05B 33/0869* (2013.01); *F21Y 2115/10* (2016.08); *F21Y 2115/30* (2016.08); *G01N 2201/0624* (2013.01); *H04N 2005/2255* (2013.01)

(58) Field of Classification Search
CPC .......... F21K 9/20; A61B 1/06; F21Y 2115/10; F21Y 2115/30; G01N 2201/0624; H04N 5/2256; H04N 2005/2255
See application file for complete search history.

(56) References Cited

U.S. PATENT DOCUMENTS

| | | | |
|---|---|---|---|
| 2011/0069163 A1 | 3/2011 | Ozawa et al. | |
| 2013/0188381 A1* | 7/2013 | Kotani | H01L 33/54 362/517 |
| 2014/0125231 A1 | 5/2014 | Nishio et al. | |
| 2014/0293651 A1 | 10/2014 | Ito et al. | |
| 2015/0108523 A1* | 4/2015 | Kotani | H01L 33/58 257/98 |
| 2015/0115278 A1* | 4/2015 | Ichikawa | H01L 33/22 257/76 |
| 2016/0308099 A1* | 10/2016 | Akamatsu | H01L 33/486 |

FOREIGN PATENT DOCUMENTS

| | | |
|---|---|---|
| EP | 2 792 933 A1 | 10/2014 |
| JP | 2007-202951 A | 8/2007 |
| JP | 2007-236598 A | 9/2007 |
| JP | 2008-118635 A | 5/2008 |
| JP | 2008-132321 A | 6/2008 |
| JP | 2009-277734 A | 11/2009 |
| JP | 2011-067267 A | 4/2011 |
| JP | 2011-067268 A | 4/2011 |
| JP | 2011-200572 A | 10/2011 |
| JP | 2012-066015 A | 4/2012 |
| JP | 2013-020814 A | 1/2013 |
| JP | 2013-027432 A | 2/2013 |
| WO | 2007/135922 A1 | 11/2007 |
| WO | 2013/008853 A1 | 1/2013 |
| WO | 2013/089102 A1 | 6/2013 |

OTHER PUBLICATIONS

International Preliminary Report on Patentability together with the Written Opinion from related International Application No. PCT/JP2014/067232 dated Jan. 28, 2016.
International Search Report dated Sep. 22, 2014 issued in PCT/JP2014/067232.
Partial Supplementary European Search Report dated Feb. 2, 2017 in related European Patent Application No. 14 82 6119.1.
Chinese Office Action dated Aug. 14, 2017 in Chinese Patent Application No. 201480040053.4.
Extended Supplementary European Search Report dated May 4, 2017 in related European Patent Application No. 14 82 6119.1.
Japanese Office Action dated May 9, 2017 in Japanese Patent Application No. 2013-148454.
Chinese Office Action dated May 8, 2018 in Chinese Patent Application No. 201480040053.4.

* cited by examiner

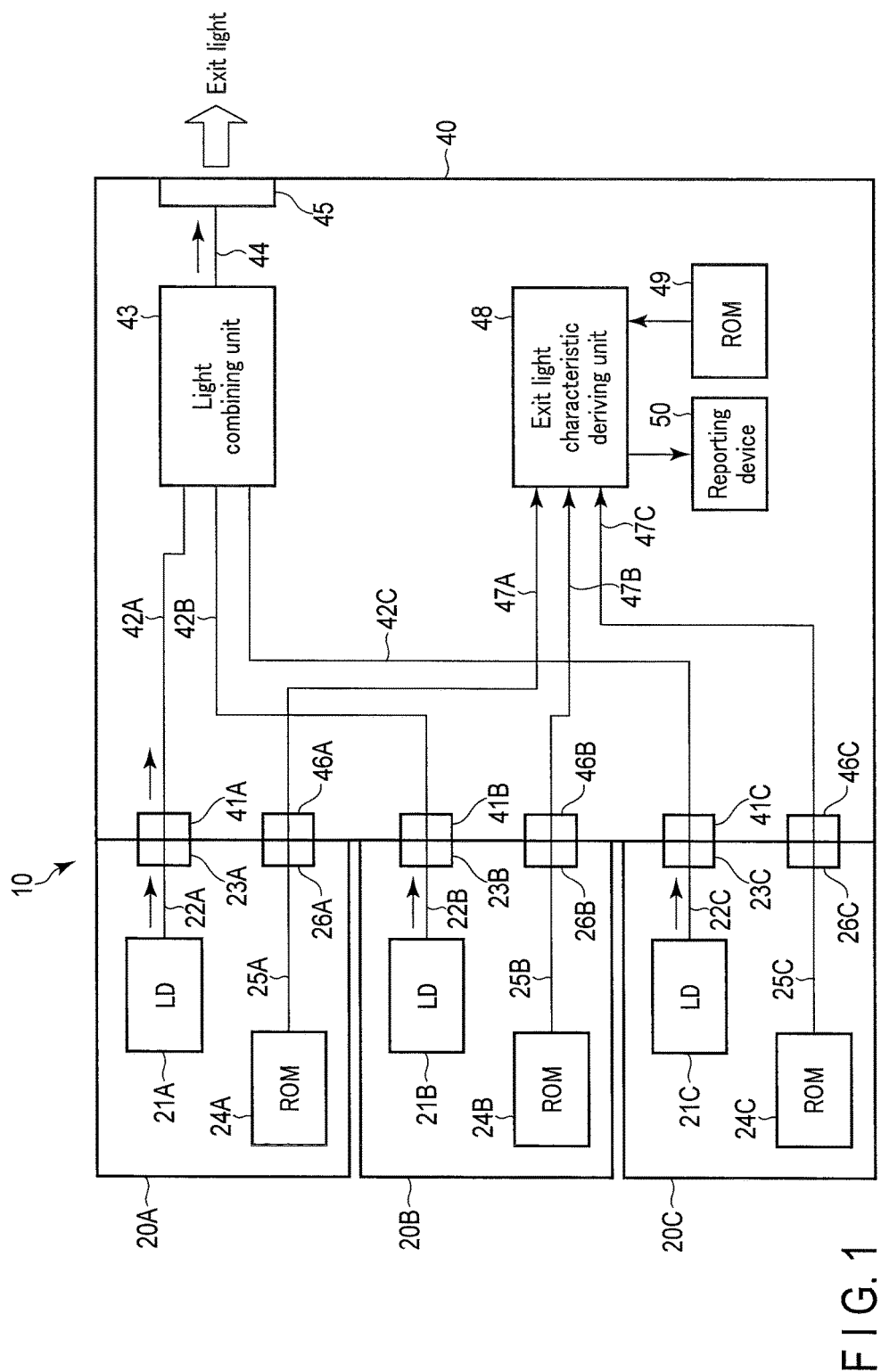
F I G. 1

LIGHT SOURCE APPARATUS

CROSS-REFERENCE TO RELATED APPLICATIONS

This application is a Continuation Application of PCT Application No. PCT/JP2014/067232, filed Jun. 27, 2014 and based upon and claiming the benefit of priority from Japanese Patent Application No. 2013-148454, filed Jul. 17, 2013, the entire contents of all of which are incorporated herein by reference.

BACKGROUND OF THE INVENTION

1. Field of the Invention

The present invention relates to a light source apparatus.

2. Description of the Related Art

In recent years, a light source apparatus that guides light emitted from a semiconductor light source by a guide member, converts color and luminous intensity distribution by a light conversion member at a tip of the guide member, and emits the converted light, has been used in observation instruments such as an endoscope. There is an effort underway to improve viewability of an observation object by properly selecting a peak wavelength and spectral shape in such a light source apparatus. In order to generate observation light for various purposes, semiconductor light sources with different wavelength characteristics are used in combination to combine light of the light sources and cause it to exit, or further wavelength-convert the combined light and cause it to exit by a wavelength conversion member, such as a fluorescent, provided at a tip of the apparatus.

For example, Jpn. Pat. Appln. KOKAI Publication No. 2009-277734 proposes a light source apparatus that combines light emitted from semiconductor light sources by an optical coupler, and then wavelength-converts the combined light by a light conversion member, so as to cause observation light for an intended purpose to exit.

BRIEF SUMMARY OF THE INVENTION

The light source apparatus of the present invention includes a main unit, light source modules attachable to and detachable from the main unit, and storage mediums to store characteristic information of the light source modules. Each light source module includes at least one light source and a light connection part to be optically connected to the main unit. The main unit includes entrance parts to be optically connected to the light connection parts of the connected light source modules, a light combining unit to combine light entering the entrance parts, an exit part to cause light combined by the light combining unit to exit, and an exit light characteristic deriving unit to derive characteristic information of achievable exit light based on characteristic information of the light source modules stored in the storage mediums.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 1 is a block diagram of a light source apparatus of a first embodiment.

DETAILED DESCRIPTION OF THE INVENTION

Figure 2:
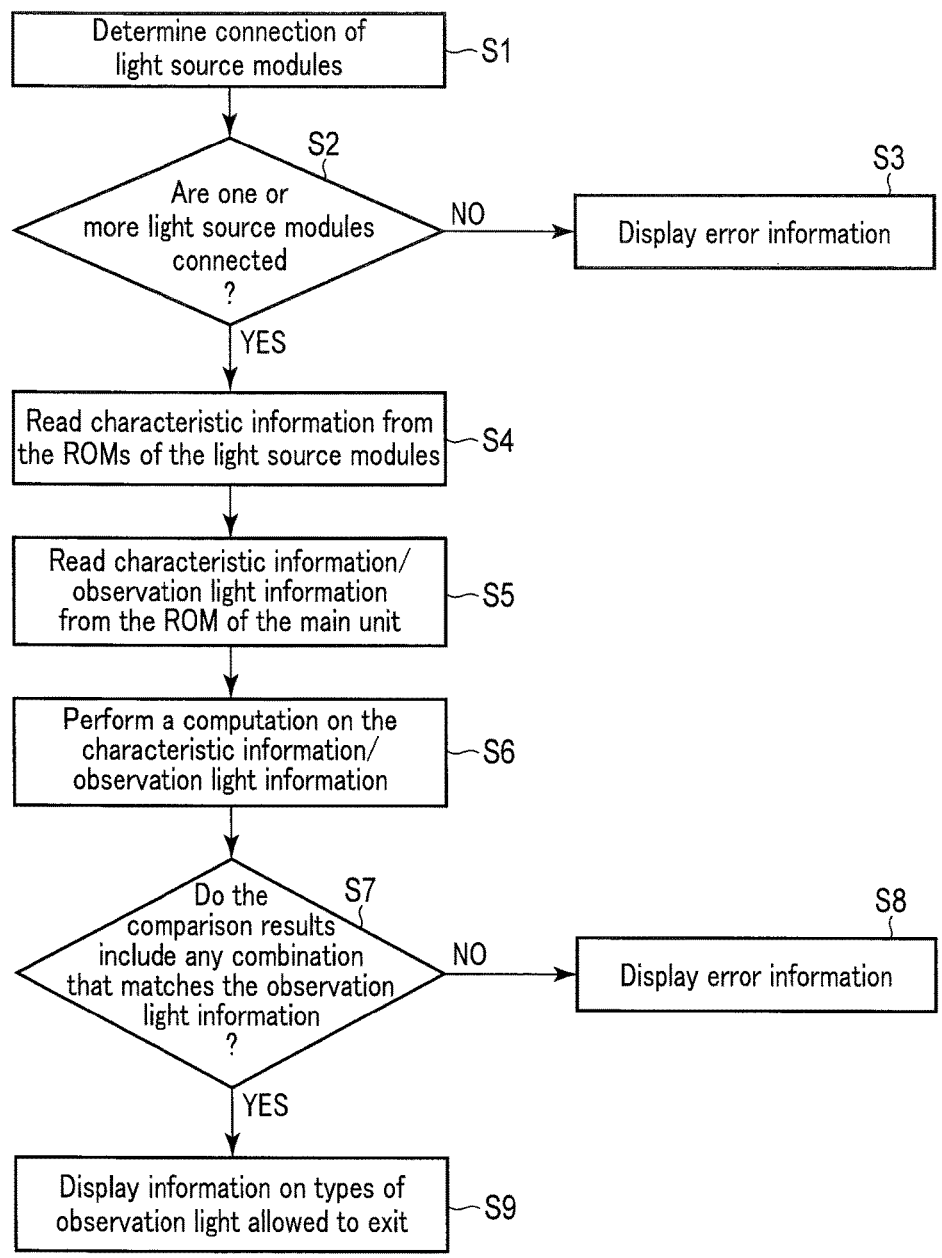
FIG. 2 shows an operational flow of the light source apparatus of the first embodiment.

Hereinafter, embodiments will be described with reference to the drawings.

First Embodiment

[Constitution]

FIG. 1 is a block diagram of the present embodiment. A light source apparatus 10 includes a main unit 40 and light source modules 20A, 20B, and 20C attachable to and detachable from the main unit 40. In this embodiment, three light source modules 20A, 20B, and 20C are attachable to and detachable from the main unit 40, but two, or four or more light source modules may be attachable to and detachable therefrom. The three light source modules 20A, 20B, and 20C are selected from a number of light source modules in accordance with the type of required observation light. Herein, three light source modules connected to the main unit 40 are expressed as light source modules 20A, 20B, and 20C for convenience. It is not always required that three light source modules 20A, 20B, and 20C are attached to the main unit 40. Depending on the observation light, the light source apparatus 10 may be used with one of the light source modules 20A, 20B, and 20C detached.

The light source modules 20A, 20B and 20C each include at least one semiconductor light source 21A, 21B, and 21C, an optical connection part 23A, 23B, and 23C to be optically connected to the main unit 40, an optical fiber 22A, 22B, and 22C to guide light emitted from the semiconductor light source 21A, 21B, and 21C to the optical connection part 23A, 23B, and 23C, a memory, such as a ROM 24A, 24B, and 24C, which is a storage medium storing characteristic information of the light source module 20A, 20B, and 20C, an electrical connection part 26A, 26B, and 26C to be electrically connected to the main unit 40, and a signal line 25A, 25B, and 25C to send an electric signal between the ROM 24A, 24B, and 24C and the electrical connection part 26A, 26B, and 26C.

Each semiconductor light source 21A, 21B, and 21C may comprise a laser diode (LD). The semiconductor light sources 21A, 21B, and 21C have different optical characteristics, such as peak wavelengths.

For example, the ROMs 24A, 24B, and 24C respectively store wavelength characteristic information, such as a peak wavelength, a line width, and a spectral shape of output light of the light source modules 20A, 20B, and 20C.

The main unit 40 includes entrance parts 41A, 41B, and 41C to be optically connected to the optical connection parts 23A, 23B, and 23C of the light source modules 20A, 20B, and 20C, optical fibers 42A, 42B, and 42C to guide light entering the entrance parts 41A, 41B, and 41C, a light combining unit 43, such as an optical combiner, to combine light guided by the optical fibers 42A, 42B, and 42C, an optical fiber 44 to guide light combined by the light combining unit 43, and an exit part 45 to cause light guided by optical fiber 44 to exit outside.

The main unit 40 also includes electrical connection parts 46A, 46B, and 46C to be electrically connected to the electrical connection parts 26A, 26B, and 26C of the light source modules 20A, 20B, and 20C, an exit light characteristic deriving unit 48 to derive characteristic information of achievable exit light, signal lines 47A, 47B, and 47C to send electric signals between electrical connection parts 46A, 46B, and 46C and the exit light characteristic deriving unit 48, a memory, such as a ROM 49, which is a storage medium storing information necessary to derive characteristic information of exit light; and a reporting device 50 to report characteristic information of exit light derived by the exit light characteristic deriving unit 48 to the outside.

The ROM 49 stores light combination characteristic information, such as transmittance including wavelength dependency with respect to light input to each input port of the light combining unit 43, observation light information such as light spectrum characteristic information to achieve the type of observation light for an intended purpose, and others. The type of observation light refers to variations including, for example, white light that can be achieved by combining three or more wavelengths including blue, green, and red, and NBI specific light to facilitate detection of cancer or the like by the observation of blood vessels with better contrast by using two wavelengths of blue-purple and green that are easily absorbed by hemoglobin in blood. The type of observation light is not limited to the above. The ROM 49 can store various types of observation light for various observation purposes. Regarding the light spectrum characteristic, an ideal spectrum characteristic and a predetermined allowable range of a characteristic deviation from the ideal spectrum characteristic are defined.

The exit light characteristic deriving unit 48 has a function of reading out information stored in the ROM 49 in the form of an electric signal, and a function of reading out information stored in the ROMs 24A, 24B, and 24C in the light source modules 20A, 20B, and 20C in the form of the electric signal. The exit light characteristic deriving unit 48 also has a function of performing a computation on the characteristic information of the light source modules 20A, 20B, and 20C and the light combination characteristic information, to derive characteristic information of exit light that is achievable by combinations of the light source modules 20A, 20B, and 20C connected to the main unit 40.

The reporting device 50 may comprise, for example, a display to image-display information.

When the light source modules 20A, 20B, and 20C are connected to the main unit 40, the semiconductor light sources 21A, 21B, and 21O are optically connected to the light combining unit 43 through optical fibers 22A, 22B, and 22C, the optical connection parts 23A, 23B, and 23C, the entrance parts 41A, 41B, and 41C, and the optical fibers 42A, 42B, and 42C, so that the light combining unit 43 can receive output light of the light source modules 20A, 20B, and 20C. The ROMs 24A, 24B, and 24C are electrically connected to the exit light characteristic deriving unit 48 through the signal lines 25A, 25B, and 25C, the electrical connection parts 26A, 26B, and 26C, electrical connection parts 46A, 46B, and 46C, and the signal lines 47A, 47B, and 47C, so that the exit light characteristic deriving unit 48 can read out stored information from the ROMs 24A, 24B, and 24C.

[Operation]

FIG. 2 shows a basic operational flow of the light source apparatus of the present embodiment. It is generally desirable that this operational flow be performed when the apparatus is powered on, but it may be performed at any instructed time.

In operation steps S1-S3, it is determined whether the light source modules 20A, 20B, and 20C are connected to respective connection ports of the main unit 40. An information reading operation is performed on each of the ROMs 24A, 24B, and 24C of the light source modules 20A, 20B, and 20C, and when information cannot be acquired, it is determined that it is not connected. When none of the light source modules 20A, 20B, and 20C are connected to the connection ports, the exit light characteristic deriving unit 48 reports, through the reporting device 50, that the light source modules 20A, 20B, and 20C are not connected.

If it is determined that one or more light source modules 20A, 20B, and 20C are connected, characteristic information is read out from the respective ROMs 24A, 24B, and 24C in step S4. In the light source apparatus 10 of FIG. 1, information of the spectral shape of output light of each of the light source modules 20A, 20B, and 20C stored in the ROMs 24A, 24B, and 24C is read out. In step S5, information stored in the ROM 49 of the main unit 40, such as transmittance of exit light with respect to light entering each entrance part 41A, 41B, and 41C, and information of a wavelength construction of the type of observation light defined by a predetermined wavelength construction are read out. In steps S6 and S7, an operation is performed on spectrum information of output light of the light source modules 20A, 20B, and 20C obtained from the ROMs 24A, 24B, and 24C, and information on transmittance obtained from the ROM 49 in all possible combinations, and comparisons are made to determine whether there is any operation result that falls within an allowable range of the predetermined wavelength construction of observation light. If there is no operation result that falls within the range of the predetermined wavelength construction, the operation proceeds to step S8, and the reporting device 50 reports that there is no observation light that can be used.

If there is an operation result that falls within the range of the predetermined wavelength construction, the operation proceeds to step S9, and the reporting device 50 reports information on types or wavelength constructions of observation light that is allowed to exit.

[Effect]

This constitution achieves a light source apparatus in which the light source modules 20A, 20B, and 20C are separately replaceable, and that can automatically derive observation light that is allowed to exit by a combination of the light source modules 20A, 20B, and 20C. Deriving all observation light achievable by combinations of the light source modules 20A, 20B, and 20C allows each light source module 20A, 20B, and 20C to be used for a plurality of observation purposes. In addition, combination errors caused when a user replaces the light source modules 20A, 20B, and 20C can be detected, and safety issues caused by an unintended exit of light can be prevented. The number of exit part 45 is not limited to one, and exit parts 45 may be provided.

First Modification of First Embodiment

[Constitution]

Figure 3:
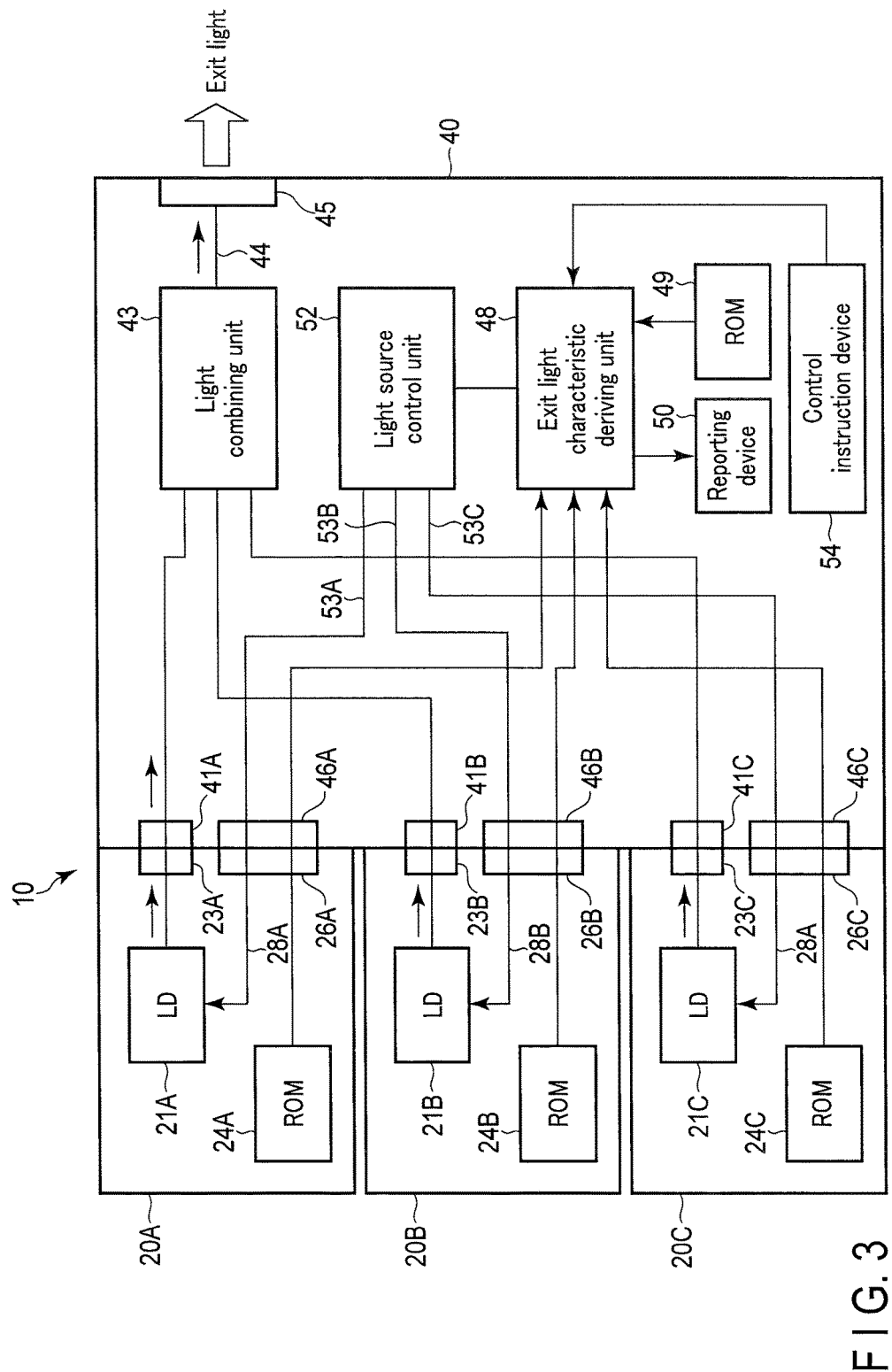
FIG. 3 is a block diagram of a light source apparatus of a first modification of the first embodiment.

FIG. 3 is a block diagram of a first modification of the first embodiment. In the figure, the same members as those shown in FIG. 1 are assigned with the same reference numerals as those shown in FIG. 1, and detailed descriptions thereof are omitted. The following descriptions will be provided while placing importance on the parts different from those in FIG. 1. The parts not described below are the same as those in the first embodiment.

In the present modification, the main unit 40 further comprises a light source control unit 52 that can separately control the semiconductor light sources 21A, 21B, and 21C, and a control instruction device 54 to allow a user to instruct an operation of the light source apparatus 10. The light source control unit 52 and the control instruction device 54 are connected to the exit light characteristic deriving unit 48. The light source control unit 52 is electrically connected to electrical connection parts 46A, 46B, and 46C through control lines 53A, 53B, and 53C.

The semiconductor light sources 21A, 21B, and 21C of the light source modules 20A, 20B, and 20C are electrically connected to electrical connection parts 26A, 26B, and 26C through the control lines 28A, 28B, and 28C, respectively.

When the light source modules 20A, 20B, and 20C are connected to the main unit 40, the semiconductor light sources 21A, 21B, and 21C are electrically connected to the light source control unit 52 through control lines 28A, 28B and 28C, electrical connection parts 26A, 26B, and 26C, electrical connection parts 46A, 46B, and 46C, and control lines 53A, 53B, and 53C, so that the light source control unit 52 can control the semiconductor light sources 21A, 21B, and 21C.

[Operation]

A user can select a type and characteristic of observation light through the control instruction device 54 and give an instruction of an exit of observation light based on the exit light characteristic reported by the reporting device 50. When there are combinations meeting the allowable characteristic range of the selected exit light, the most suitable combination may be automatically or manually selected as observation light based on wavelength information. The exit light characteristic deriving unit 48 determines whether the selected type of observation light is achievable based on the characteristic information of the derived achievable exit light. If it is determined that the selected type is not achievable, the reporting device 50 makes a report to that effect, and does not drive any light source. If it is determined that the selected type is achievable, the light source control unit 52 controls the semiconductor light sources 21A, 21B, and 21C, causing observation light of the selected type to exit.

[Effect]

This structure enables collective control for placing the light source modules 20A, 20B, and 20C in proper operation states, and facilitates obtaining observation light for an intended purpose.

Second Modification of First Embodiment

[Constitution]

In the present modification, the ROMs 24A, 24B, and 24C of the light source modules 20A, 20B, and 20C store information necessary for light quantity control, i.e., light quantity control characteristic information, in addition to the wavelength characteristic information of the light source modules 20A, 20B, and 20C. The light quantity control characteristic information is, for example, a correlation table of output light quantity of the light source modules 20A, 20B, and 20C and drive currents of the included semiconductor light sources 21A, 21B, and 21C, threshold currents of the semiconductor light sources, light quantity-input current functions, maximum output light quantity, and rated light quantity. In the case of pulse driving, the light quantity control characteristic information may include information on the maximum pulse drive frequency necessary for control of the semiconductor light sources 21A, 21B, and 21C or the like.

[Operation]

The exit light characteristic deriving unit 48 performs a computation on characteristic information of achievable exit light including light source module control information. For example, the exit light characteristic deriving unit 48 derives the maximum light quantity of exit light of the case where output light of the light source modules 20A, 20B, and 20C are mixed by a constant fraction to achieve any type of observation light, i.e., derives the maximum light quantity of exit light that is allowed to exit while maintaining a predetermined wavelength construction, and reports the information by the reporting device 50. The exit light characteristic deriving unit 48 also calculates a color rendering index of exit light that can be achieved when output light of the light source modules 20A, 20B, and 20C is mixed by a fraction within a certain range, and reports the information by the reporting device 50. The color rendering index is derived from the wavelengths and maximum light intensities of the light entering the entrance parts 41A, 41B, and 41C. In the case of pulse driving the light source, the exit light characteristic deriving unit 48 compares the maximum pulse frequencies between the light source modules 20A, 20B, and 20C and reports, by the reporting device 50, the lowest maximum pulse frequency as a pulse drive frequency applicable to exit light from the exit part 45. If there are combinations that are allowed to exit as any observation light, a combination may be automatically or manually selected by giving priority to one of the characteristics, such as the color rendering index, and the maximum light quantity achievable by a combination.

[Effect]

This constitution clarifies not only types of exit light used as observation light, but also a achievable characteristic range, and enables obtaining exit light with characteristics more suitable for observation light.

(Other Modifications)

Figure 4:
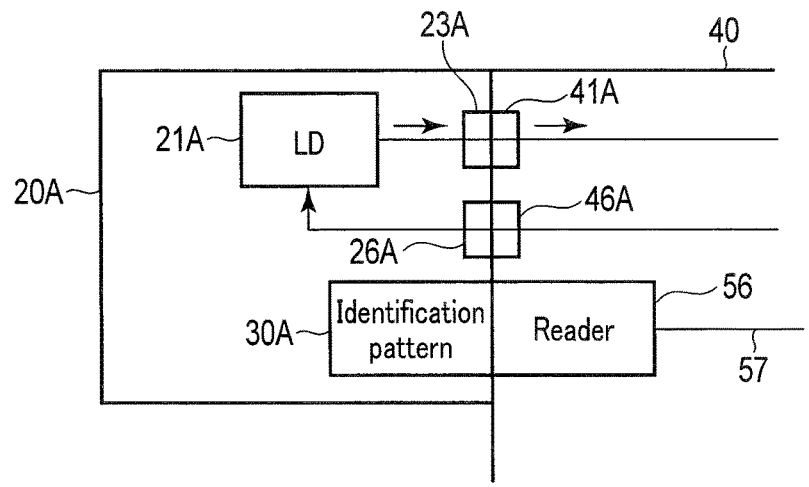
FIG. 4 is a block diagram of a part of a light source apparatus of another modification of the first embodiment.

In the constitution example shown in FIG. 1, the storage mediums storing characteristic information of the light source modules 20A, 20B, and 20C comprise the ROMs 24A, 24B, and 24C. However, the storage mediums are not limited to the ROMs 24A, 24B, and 24C. For example, as shown in FIG. 4, a storage medium storing characteristic information of the light source module 20A may comprise an identification pattern 30A such as an optically-identifiable reflection pattern, like a bar code, or a mechanically-identifiable concave-convex pattern. In this case, the main unit 40 includes a reader 56 to optically or mechanically read characteristic information of the light source module 20A stored in the identification pattern 30A. The reader 56 outputs an electric signal of characteristic information of the light source module 20A to the exit light characteristic deriving unit 48 through signal line 57.

Figure 5:
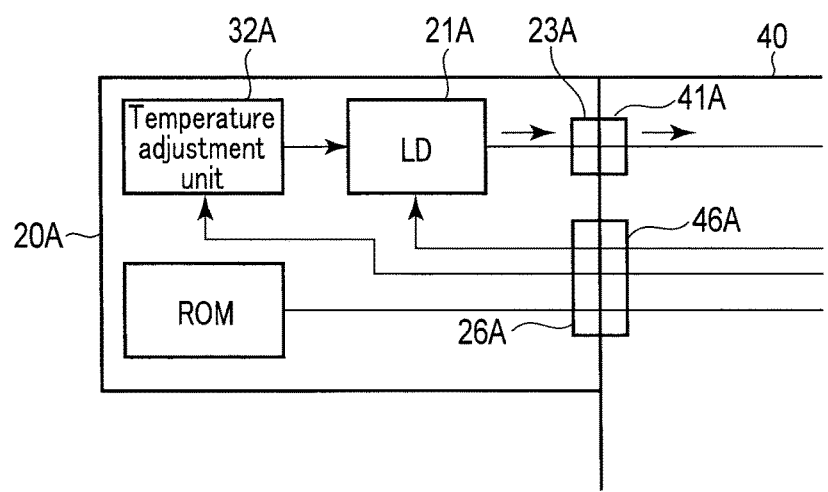
FIG. 5 is a block diagram of a part of a light source apparatus of still another modification of the first embodiment.

Information stored in the ROMs 24A, 24B, and 24C and the ROM 49 may be not only optical information, but also thermal information or the like. For example, wavelength characteristic information and light quantity control characteristic information may be information that includes light source temperature dependency of the characteristic. As shown in FIG. 5, the light source module 20A may include a temperature adjustment unit 32A to adjust the temperature of the semiconductor light source 21A. The temperature adjustment unit 32A keeps the semiconductor light source 21A at a preset temperature. The exit light characteristic deriving unit 48 derives characteristic information of exit light with reference to the preset temperature of the temperature adjustment unit 32A, and light source temperature dependency of each of the wavelength characteristic information and the light quantity characteristic information. Specifically, the exit light characteristic deriving unit 48 reads out information corresponding to the preset temperature as each of the wavelength characteristic information and light quantity characteristic information, and derives characteristic information of exit light including amended temperature dependency of the semiconductor light source 21A. Accordingly, more stable exit light is obtained.

Detailed characteristic information of the light source modules 21A-200 need not be stored in the ROMs 24A, 24B, and 24C in the light source modules 20A-20C, and may be stored, for example, in the ROM 49 in the main unit 40. In other words, the main unit 40 may include a storage medium storing characteristic information of the light source modules 20A-20C. In this case, the light source modules 20A-20C only need to have self-identification information. Such information may be held in the light source modules 20A-20C in the form of, for example, an identification pattern.

Each semiconductor light source 21A, 21B, and 21C includes one semiconductor light source, but may include two or more semiconductor light sources. For example, each semiconductor light source 21A, 21B, and 21C may include a plurality of semiconductor light sources corresponding to a type of observation light and may cause light from the semiconductor light sources selectively or in combination to exit.

When there is a deficiency in the combination of the light source modules 20A, 20B, and 20C for a type and characteristic of observation light designated by a user, a deficient optical characteristic or a type of light source module may be derived and information thereof may be reported by the reporting device 50.

As the reporting device to report information to a user, various known reporting devices such as a visual reporting device to utilize an image or lighting of a lamp, and a reporting device to utilize sound may be used. The main unit 40 may include a function of preventing an erroneous operation by locking an operation unit of an interface upon detection of an error.

Instead of the main unit 40 including the light source control unit 52, each light source module 20A, 20B, and 20C may have a similar function.

ROM 49 in the main unit 40 may be easily replaceable, and may be replaced with a new ROM including information on observation light or a new light source module.

Second Embodiment

[Structure]

Figure 6:
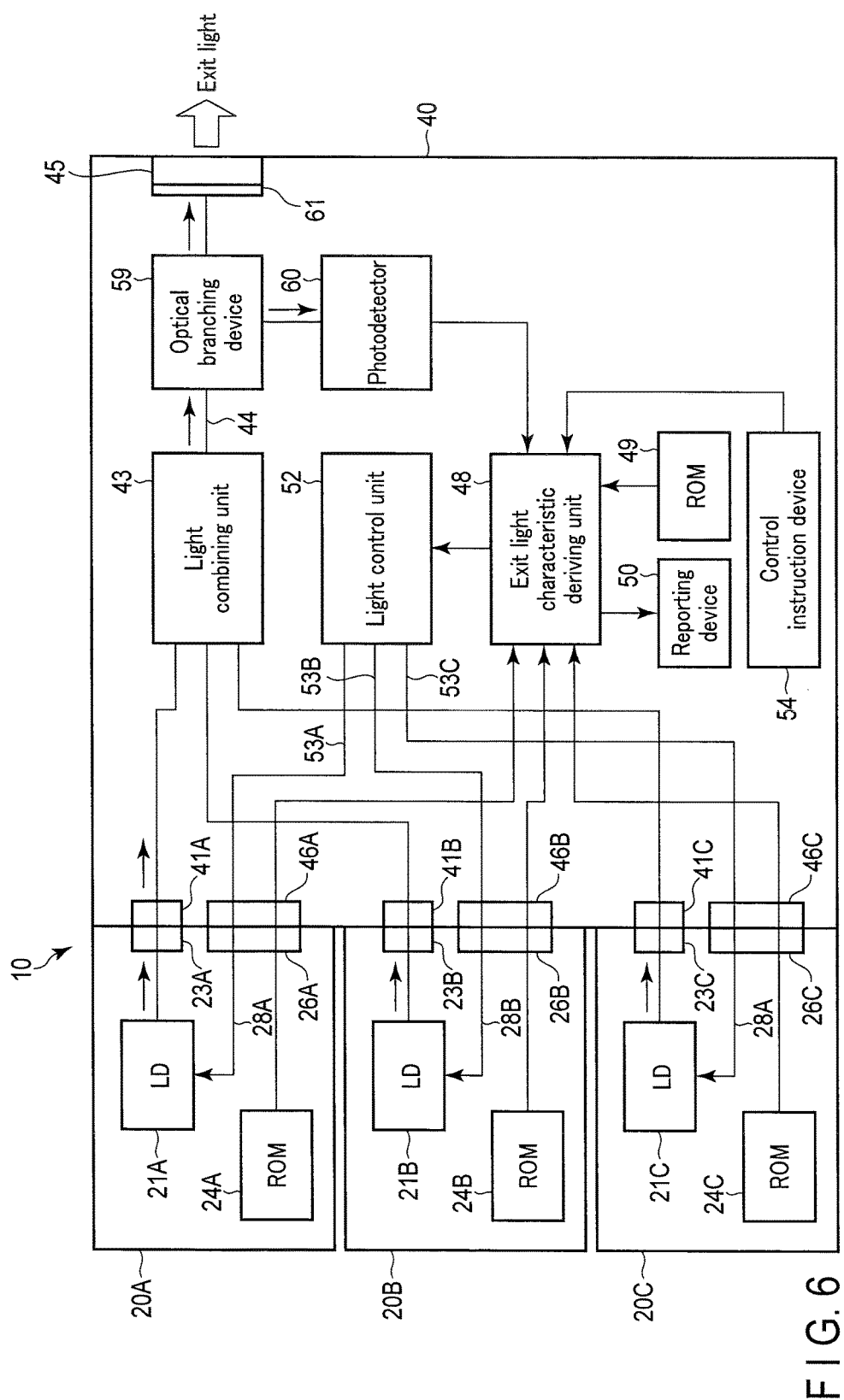
FIG. 6 is a block diagram of a light source apparatus of a second embodiment.

FIG. 6 is a block diagram of a second embodiment. In the present embodiment, the main unit 40 includes an optical branching device 59 to branch light combined by the light combining unit 43, and a photodetector 60 to detect light combined by the light combining unit 43. The optical branching device 59 is located between the light combining unit 43 and the exit part 45, guides part of light from the light combining unit 43 to the photodetector 60, and the remaining part of the light to the exit part 45. The photodetector 60 detects a characteristic such as light quantity of incident light, and outputs an electric signal indicating the light quantity to the exit light characteristic deriving unit 48. The exit light characteristic deriving unit 48 derives characteristic information of exit light of the light source apparatus 10 based on the characteristic, such as light quantity, of the light detected by the photodetector 60.

The main unit 40 includes a light-blocking shutter 61 placed in front of the exit part 45. The light-blocking shutter 61 performs switching between exiting and blocking of light guided to the exit part 45 by closing and opening of the light-blocking shutter 61.

The ROMs 24A, 24B, and 24C of the light source modules 20A, 20B, and 20C store characteristic variation allowable values in addition to characteristic information of the light source modules 20A, 20B, and 20C described in the first embodiment, and the ROM 49 of the main unit 40 stores a branching ratio of the optical branching device 59.

[Operation]

In the present embodiment, the exit light characteristic deriving unit 48 uses light quantity information detected by the photodetector 60 to derive characteristic information of exit light. Desirably, the exit light characteristic deriving unit 48 uses stored information in the ROMs 24A, 24B, and 24C in addition to light quantity information detected by the photodetector 60 to derive characteristic information of exit light.

As in the first embodiment, an information reading operation is performed on the ROMs 24A, 24B, and 24C to confirm whether the light source modules 20A, 20B, and 20C are connected. With the light-blocking shutter 61 closed, the light source modules 20A, 20B, and 20C are separately controlled to emit light while changing the light quantity by changing the control current. The photodetector 60 detects output light quantity of each light source module 20A, 20B, and 20C and sends the information to the exit light characteristic deriving unit 48. The light exit light characteristic deriving unit 48 amends a light quantity characteristic based on the difference between the stored light quantity and the detected light quantity to derive characteristic information of exit light, such as a color rendering index, maximum light quantity, and a type of achievable observation light.

[Effect]

This constitution is capable of amending temporal characteristic variations of, for example, the semiconductor light sources 21A, 21B, and 21C and light connection parts 23A, 23B, and 23C, and always deriving observation light with the best combination ratio.

(Modifications)

As in the first embodiment, a user can control a light source through the control instruction device 54 based on the derived optical characteristic. At the time of an exit, the light-blocking shutter is opened. During observation, the photodetector 60 can keep monitoring the light quantity, and can amend outputs of the light source modules 20A, 20B, and 20C when there is a difference between the instructed characteristic value and the detected value.

The photodetector 60 can also be used as an abnormality detection means of the light source modules 20A, 20B, and 200. When the detected light quantity takes a value other than the allowable characteristic variation values, it is possible to determine that there is an abnormality in a light source module 20A, 20B, and 20C or an optical connection condition, to report it by the reporting device, and to stop the operation of the light source.

In the present embodiment, exit is prevented by the light-blocking shutter 61 when light quantity is detected. However, it is possible to perform light detection with light quantity within a safety range even if light exits the exit part 45 when light quantity is detected, and to make an amendment by prediction based on the information, without employing the light-blocking shutter 61.

Figure 7:
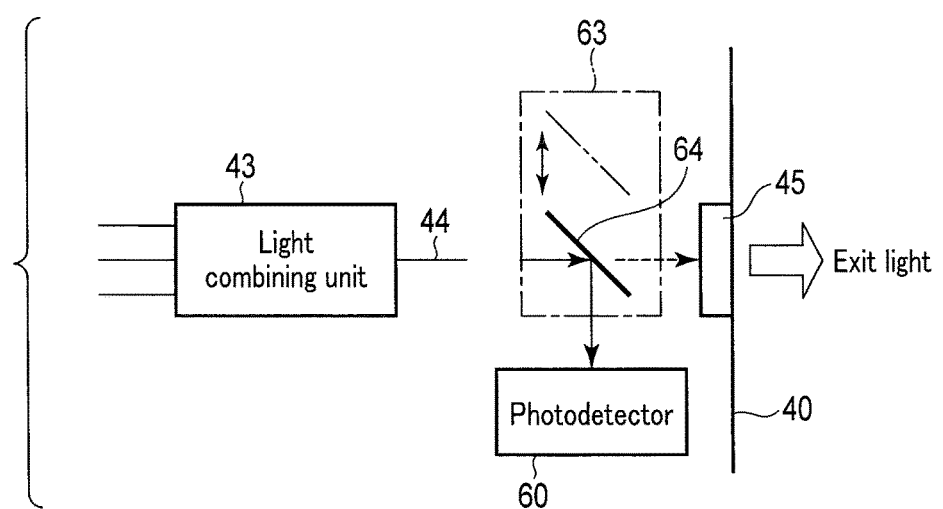
FIG. 7 is a block diagram of a part of a light source apparatus of a modification of the second embodiment.

In the present embodiment, the main unit 40 includes an optical branching device 59 to branch part of light combined by the light combining unit 43 and guide the bifurcated part to the photodetector 60, but may include a switching device 63 to switch a guided destination of light combined by the light combining unit 43 between the exit part 45 and the photodetector 60, as shown in FIG. 7. The switching device 63 includes a movable mirror 64 that is allowed to be inserted on and removed from an optical path between the optical fiber 44 and the exit part 45. During detection, the movable mirror 64 is placed on the optical path and guides light from the optical fiber 44 to the photodetector 60. During observation, the movable mirror 64 is moved out of the optical path and guides light from the optical fiber 44 to the exit part 45. The switching device 63 usually, for example, when power is turned on, guides light to the optical detector 60, and in that condition, detection of light quantity of the exit light and deriving of characteristic information are performed. After an exit instruction, the switching device 63 switches a guided destination of light to the exit part 45, thereby causing light to exit the light source apparatus 10. This constitution can prevent a reduction of light quantity of exit light due to light branching. In addition, direct detection of exit light enables accurate amendment of characteristic values.

In the present embodiment, the photodetector 60 is a detector to detect light quantity, but may be a detector capable of detecting a wavelength characteristic as well as the light quantity. This constitution enables reference to the actual output power for the wavelength characteristic, and enables stricter amendment of output power.

Third Embodiment

[Constitution]

Figure 8:
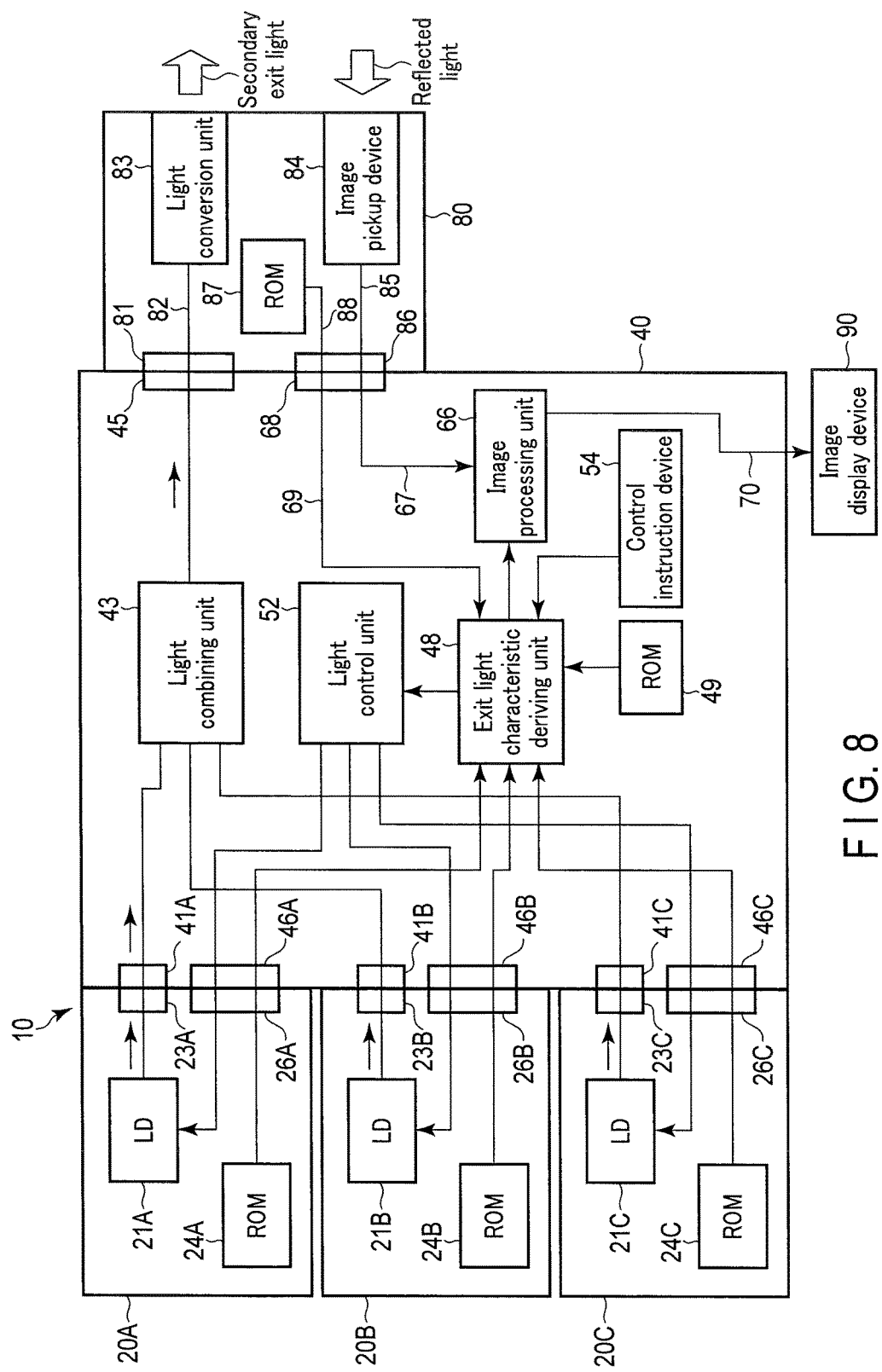
FIG. 8 is a block diagram of a light source apparatus of a third embodiment.

FIG. 8 is a block diagram of a third embodiment. In the present embodiment, an endoscope 80, which is an illuminating unit, is connected to the exit part 45 of the light source apparatus 10. The endoscope 80 includes a scope entrance part 81 to be optically connected to the exit part 45 of the main unit 40, an optical fiber 82 to guide light entering the scope entrance part 81, and a light conversion unit 83 to perform light conversion processing, such as wavelength conversion or diffusion, on the light guided by the optical fiber 82 and cause the light to exit outside as secondary exit light.

The endoscope 80 also includes an image pickup device 84 to receive reflected light from an observation object and acquire image information, an electrical connection part 86 electrically connected to the main unit 40, a signal line 85 to send the image information between the image pickup device 84 and the electrical connection part 86, a ROM 87 that is a storage medium storing characteristic information of the endoscope 80, and a signal line 88 to send an electric signal between the ROM 87 and the electrical connection part 86. The ROM 87 stores information on light conversion characteristics of the light conversion unit 83, such as a wavelength conversion characteristic, a light dispersion conversion characteristic, and an allowable incident light quantity set that depends on the limit to the amount of heat generation, and characteristic information of the image pickup device 84.

The main unit 40 includes an electrical connection part 68 to be electrically connected to the electrical connection part 86 of the endoscope 80, an image processing unit 66 to perform image processing suitable for observation purposes of the image acquired by the image pickup device 84, a signal line 67 to send an electric signal between the electrical connection part 68 and the image processing unit 66, and a signal line 69 to send an electric signal between the electrical connection part 68 and the exit light characteristic deriving unit 48.

The image processing unit 66 is electrically connected, through a signal line 70, to an image display device 90 such as an external monitor. The image display device 90 displays a result of the processing by the image processing unit 66.

[Operation/Effect]

In the present embodiment, the exit light characteristic deriving unit 48 derives characteristic information of secondary exit light by a computation based on characteristic information of the endoscope 80 as well as characteristic information of the light source modules 20A, 20B, and 20C, and characteristic information of the main unit 40. This enables deriving of the observation light necessary for endoscope observation. The exit light characteristic deriving unit 48 also derives an achievable image processing mode based on image acquisition characteristic information and characteristic information of the secondary exit light. This enables acquisition of an image suitable for endoscope observation.

The exit light characteristic deriving unit 48 is also capable of detecting an improper correspondence between the endoscope 80 and a combination of the light source modules 20A, 20B, and 20C by referring to information. In the light conversion unit 83, an allowable incident light quantity is set. A failure in the endoscope 80 can be prevented by controlling the light source modules 20A, 20B, and 20C so that the light quantity of the exit light from the main unit 40 does not exceed the allowable light quantity.

In addition, it is possible to automatically execute suitable image processing settings based on the type or characteristic of the secondary exit light, and to perform the most suitable image processing together with light source control.

In the present embodiment, the main unit 40 includes the image processing unit 66. Alternatively, for example, an image processing device may be provided outside the light source apparatus 10, and image information from the endoscope 80 may be processed in the image processing device. Similarly, part of the other constituent functions may be separately provided outside the main unit 40.

While certain embodiments of the present invention have been described with reference to the drawings, the present invention is not limited thereto, and may be modified or altered without departing from the spirit of the invention. The modification or alteration mentioned herein includes proper combinations of the aforesaid embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source apparatus comprising:
a main unit;
light source modules attachable to and detachable from the main unit; and
storage mediums storing characteristic information of the light source modules,
each light source module including at least one light source and a light connection part to be optically connected to the main unit, and
the main unit including entrance parts to be optically connected to the light connection parts of the connected light source modules, a light combining unit to combine light entering the entrance parts, at least one exit part to cause light combined by the light combining unit to exit, and an exit light characteristic deriving unit to derive characteristic information of achievable exit light based on characteristic information of the light source modules stored in the storage mediums.

2. The light source apparatus according to claim 1, wherein the characteristic information of the light source modules includes wavelength characteristic information including at least one of a peak wavelength, a line width, and a spectral shape of output light of the light source modules.

3. The light source apparatus according to claim 1, wherein the characteristic information of the light source modules includes light quantity control characteristic information including at least one of a threshold current, a light quantity-input current function, and a maximum output light quantity of the light sources.

4. The light source apparatus according to claim 1, wherein the characteristic information of the light source modules includes a maximum pulse drive frequency of the light sources.

5. The light source apparatus according to claim 2, wherein the characteristic information of the light source modules includes information on light source temperature dependency of each characteristic of the light source modules.

6. The light source apparatus according to claim 2, wherein the characteristic information of the exit light includes information on a wavelength construction of exit light that is achievable by a combination of the light source modules.

7. The light source apparatus according claim 2, wherein the characteristic information of the exit light includes a maximum light quantity of exit light that is able to exit while keeping a predetermined wavelength construction.

8. The light source apparatus according to claim 2, wherein the characteristic information of the exit light includes a color rendering index of the exit light from the exit part, the color rendering index being derived from a wavelength and a maximum light quantity of the light entering the entrance part.

9. The light source apparatus according to claim 2, wherein the characteristic information of the exit light includes a pulse drive frequency applicable to the exit light from the exit part.

10. The light source apparatus according to claim 6, wherein
the light source module includes a temperature adjustment unit to adjust a temperature of the light source, and
the characteristic information of the exit light is derived with reference to a preset temperature of the temperature adjustment unit, and light source temperature dependency of each of wavelength characteristic information and light quantity characteristic information.

11. The light source apparatus according to claim 2, wherein the storage mediums comprise memories provided in at least one of the light source modules and the main unit, and the exit light characteristic deriving unit reads characteristic information of the light source modules from the memories.

12. The light source apparatus according to claim 2, wherein the storage mediums comprise identification patterns provided in the light source modules, and the main unit includes a reader to read characteristic information of the light source modules from the identification patterns and output the characteristic information to the exit light characteristic deriving unit.

13. The light source apparatus according to claim 1, wherein the storage mediums stores observation light characteristic information on optical characteristics of exit light required for observation light, and the exit light characteristic deriving unit determines whether exit light meeting the observation light characteristic information presents in the achievable exit light or not based on the characteristic information of the light source modules stored in the storage mediums.

14. The light source apparatus according claim 13, wherein the storage mediums stores light combination characteristic information on optical characteristics of light transmitted through the light combining unit, and the exit light characteristic deriving unit determines whether exit light meeting the observation light characteristic information presents in the achievable exit light or not based on the characteristic information of the light source modules and the light combination characteristic information stored in the storage mediums.

15. The light source apparatus according claim 13, wherein the main unit further includes a reporting device to report a type or a wavelength construction of the achievable exit light meeting the observation light characteristic information, or report the absence of the achievable exit light meeting the observation light characteristic information.

16. The light source apparatus according claim 13, wherein the main unit further includes a reporting device to report information of the achievable exit light, and when the achievable exit light includes a plurality of types of light meeting the observation light characteristic information, the reporting device reports a combination and a ratio of the light source modules having a characteristic information of the exit light nearest a predetermined optical characteristic in the observation light characteristic information.

17. The light source apparatus according to claim 2, wherein the main unit includes a storage medium storing light combination characteristic information for light input to the light combining unit, and the exit light characteristic deriving unit performs a computation on the characteristic information of the light source modules and the light combining characteristic information to derive characteristic information of the exit light.

18. The light source apparatus according to claim 2, wherein the main unit includes a photodetector to detect light combined by the light combining unit, and the exit light characteristic deriving unit derives characteristic information of the exit light based on a characteristic of the light detected by the photodetector.

19. The light source apparatus according to claim 18, wherein the main unit further includes a light branching device to branch part of light combined by the light combining unit and guide the branched part to the photodetector.

20. The light source apparatus according to claim 18, wherein the main unit further includes a switching device to switch a guided destination of light combined by the light combining unit between the exit part and the photodetector.

21. The light source apparatus according to claim 2, further comprising a reporting device to report the characteristic information of the exit light.

22. The light source apparatus according to claim 2, wherein the main unit further includes a light source control unit to control the light source in each of the light source modules, and a control instruction device capable of selecting a type and characteristic of observation light to be used and giving an instruction of an exit of the observation light.

23. The light source apparatus according to claim 22, further comprising a reporting device to report a type or characteristic of a deficient light source module when there is a deficiency of a light source module for the selected type and characteristic of the observation light.

24. The light source apparatus according to claim 2, wherein
the light source apparatus is connected to an illuminating unit,
the illuminating unit includes an entrance part to be optically connected to the exit part, a light conversion unit to convert the exit light exiting the exit part into secondary exit light, and a storage medium storing light conversion characteristic information of the light conversion unit, and
the exit light characteristic deriving unit performs a computation on the characteristic information of the exit light and the light conversion characteristic information to derive characteristic information of the secondary exit light.

25. The light source apparatus according to claim 24, wherein
the illuminating unit further includes an image pickup device to acquire image information of an observation object,
the storage medium further stores image acquisition characteristic information of the image pickup device, and
the exit light characteristic deriving unit derives an achievable image processing mode based on the image acquisition characteristic information and the characteristic information of the secondary exit light.

* * * * *